United States Patent
Samide

(10) Patent No.: US 6,640,355 B1
(45) Date of Patent: Nov. 4, 2003

(54) IN-BOWL STOOL SAMPLE COLLECTION DEVICE

(76) Inventor: James A. Samide, 2733 111th Ave., NW., Coon Rapids, MN (US) 55433

( * ) Notice: Subject to any disclaimer, the term of this patent is extended or adjusted under 35 U.S.C. 154(b) by 0 days.

(21) Appl. No.: 10/236,682

(22) Filed: Sep. 6, 2002

(51) Int. Cl.7 ............................................. A47K 11/00
(52) U.S. Cl. ........................ 4/661; 4/300.3; 4/144.2; 4/DIG. 902; 604/322; 604/326
(58) Field of Search ................ 4/661, 300.3, DIG. 902, 4/144.2; 604/322, 326

(56) References Cited

U.S. PATENT DOCUMENTS

| | | | |
|---|---|---|---|
| 2,801,424 A | * 8/1957 | Mercer | 4/661 |
| 3,571,817 A | * 3/1971 | Gosnell | 4/144.1 |
| 3,718,431 A | 2/1973 | Wild | 23/230 B |
| 4,215,443 A | * 8/1980 | Babik | 4/300.3 |
| 4,309,782 A | 1/1982 | Paulin | 4/661 |
| D267,273 S | 12/1982 | Paulin | D24/57 |
| 4,445,235 A | 5/1984 | Slover et al. | 4/144.2 |
| 4,521,520 A | 6/1985 | Jacke | 436/66 |
| 4,860,767 A | 8/1989 | Maekawa | 128/760 |
| 5,337,426 A | 8/1994 | Matusewicz et al. | 4/661 |
| 5,412,819 A | 5/1995 | Matusewicz et al. | 4/661 |
| 5,463,782 A | 11/1995 | Carlson et al. | 4/661 |

* cited by examiner

Primary Examiner—Gregory L. Huson
Assistant Examiner—Azadeh Kokabi
(74) Attorney, Agent, or Firm—Nawrocki, Rooney & Sivertson, P.A.

(57) ABSTRACT

An article for collecting human feces has at least one projecting arm supporting at least a collection structure of the article within a toilet bowl above the water line therein. The collection structure of the article is disposed to receive and support the human feces for easy collection of a fecal sample.

18 Claims, 1 Drawing Sheet

IN-BOWL STOOL SAMPLE COLLECTION DEVICE

BACKGROUND OF THE INVENTION

Certain types of medical diagnostic procedures require a stool (fecal) sample. It is important to not contaminate the patient's fecal sample with urine or other materials.

As one might expect, this sample-gathering process is distasteful. Accordingly, a number of different articles to make this collection process more convenient and less distasteful have been developed. Many of these stool sample collection articles are not as convenient as one might wish. Some may allow the sample to be contaminated.

For example, one type of article design now in use at the Mayo Clinic, Rochester, Minn. has a cardboard frame with a centrally located opening. A stool collection element formed of disposable tissue and easily detachable from the frame hangs below the opening. The cardboard frame is adhesively attached to the top surface of a toilet bowl rim, and is stiff enough to support the collection element above the water line. The collection element is attached to slots in the frame in a way allowing the collection element to be easily detached from the frame. After the sample is deposited and collected, the collection element is detached from the frame and then flushed in the normal way with the remainder of the sample.

BRIEF DESCRIPTION OF THE INVENTION

I have developed an improved article for collecting a fecal sample discharged by a human into a toilet bowl. The article is to be placed within a conventional toilet bowl of the type having an inwardly sloping internal surface and a water line. The article is to be supported by the internal surface of the toilet bowl in a position allowing a fecal sample discharged by a human into the toilet bowl to be collected and supported above the water line.

The article comprises a collection structure for supporting at least a portion of the fecal sample. The collection structure has a generally planar shape. At least one support arm projects from the collection structure. I prefer that at least a portion of each arm is generally coplanar with the collection structure, although this may not be necessary. Each support arm has a tip for engaging the bowl's internal surface for supporting the collection structure above the water line.

I have developed a number of variations for this article. In one embodiment the central structure has a peripheral frame generally defining the plane. The central structure comprises a collection element formed of a plurality of bars having ends unitary with the peripheral frame. The bars may be spaced from each other and extend across the central structure to define a plurality of slots between adjacent bars, or may intersect one or more of the other bars to create a lattice pattern. For this embodiment, the patient may for example place toilet paper on the bars to assist in supporting the stool while obtaining the sample.

Another embodiment of the article may have a frame comprising three side bars, each joined at the ends to the ends of two other side bars, so as to- generally defining a triangle. A support arm projects from the joined ends of two side bars In another embodiment, the central structure may comprise a collection element such as a relatively flexible sheet having a relatively rigid peripheral frame with which each support arm is integral. The sheet may itself be integral with the peripheral frame.

DESCRIPTION OF THE PREFERRED EMBODIMENTS

Figure 1:
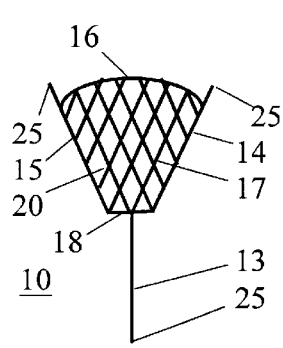
FIG. 1 is a top projective view of a first version of the article of the invention.
Figures 2A, 2B:
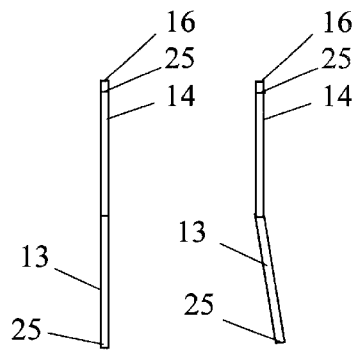
FIGS. 2a and 2b show side projective views of different versions of the article of FIG. 1.

The views of FIGS. 1 and 2a show a first embodiment of the invention as a fecal collection article 10 comprising a collection structure 20 having edge bars 14, 15, 16, 18. Edge bars 14, 15, 16, 18 are arranged with each joined to two other of the edge bars 14, 15, 16, 18 to form a generally trapezoidal structure lying in a plane, i.e., having a generally planar form. While a generally planar form is not necessary, such a form makes article 10 somewhat easier to store, ship, and use.

In FIG. 1, edge bar 16 is shown as arctuate, but may be straight as well. A number of shapes for collection structure 20 such as triangular, rather than the generally trapezoidal shape shown in FIG. 1, are also suitable. In FIG. 1, edge bars 14 and 15 have ends projecting a small amount past edge bar 16 to thereby form short arms. Edge bars 14, 15, 16, 18 are relatively rigid members.

A plurality of interior bars 17 are joined to edge bars 14, 15, 16, 18 and lie within the area defined by edge bars 14, 15, 16, 18. In the design shown, the interior bars 17 cooperate with edge bars 14, 15,16, 18 to form a lattice pattern for collection structure 20. Interior bars 17 should be close enough to each other to support or retain at least a portion of any fecal material deposited thereon, perhaps 0.5–1.0 in (1.25–2.5 cm.). A user may find it convenient to lay toilet paper on bars 17 prior to use. In that case, the article 10 can simply be tilted after removing a portion of the sample to allow the remainder of the sample and the toilet paper to slide into the toilet 30 for disposal. In this way, article 10 may be reusable.

At least one support arm 13 projects from collection structure 20, and may be integral therewith. Arm 13 has a tip 25 forming one point for supporting article 10. Arm 13 preferably has a cross section creating greater stiffness when bending out of the plane of FIG. 1 than in the plane of FIG. 1. Edge bars 14 and 15 are shown projecting past edge bar 16 so as to form two additional relatively short support arms, each also with a tip 25. Three support points assure solid support. Note that arm 13 is angularly oriented by at least 90° from the two arms formed by the extensions of edge bars 14 and 15.

Arm 13 can lie generally in the plane of collection structure 20. (FIG. 2a) or can slant in a generally acute angle from this plane (FIG. 2b). It's not clear at this point if an angled arm 13 as in FIG. 2b has any advantages in use over a planar arm 13 as shown in FIG. 2a.

Collection structure 20 and arm 13 should be stiff enough to support the weight of a typical fecal sample, perhaps several ounces (100 gm. or more). Referring to FIGS. 2a and 2b, edge bar 14 and arm 13 are shown with cross sections that are substantially deeper than they are thick, to provide adequate stiffness for opposing in-plane bending as shown in FIGS. 2a and 2b with a minimum of material. However, arm 13 must also be laterally stiff enough to avoid excessive lateral bending when supporting a fecal sample during use. A round or oval cross section is equally acceptable. I envision article 10 as molded from a suitable inexpensive plastic material that may have a relatively low modulus of elasticity, although metal such as iron may also be a suitable material from which to construct article 10. Article 10 may also be formed of a combination of metal wire and plastic.

Figure 3:
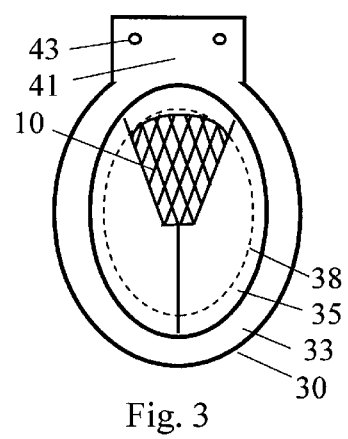
FIG. 3 shows a plan view of a toilet bowl in which the article of FIG. 1 has been placed for use.

The tip of arm 13 and the extensions of edge bars 14 and 15 at 25 are intended to support article 10 by resting on the slanted inner surface of a standard toilet bowl 30 as shown in FIG. 3 in top projective view. Such a toilet bowl 30 conventionally has a thickened rim 33 and a generally conical interior surface 35. Interior surface 35 slopes inwardly and downwardly to a drain 45 at the bottom of the bowl 30 providing for waste disposal. A rear surface 41 generally flush with rim 33 has a pair of holes 43 by which a toilet seat (not shown) may be attached. A water tank for holding flushing water is also not shown, but is attached at the rear of bowl 30 (above bowl 30 as shown in FIG. 3).

To limit escape of sewer gasses into the surrounding occupied space, toilet designs provide for diverting water during filling the tank after flushing to cover drain 45 to an inch or two (2.5 to 5 cm.). The water surface creates a water line 38 on inner surface 35.

In use, article 10 is placed within toilet bowl 30 with tips 25 engaging surface 35. The inward and downward slant of surface 35 can support an article 10 more or less parallel to and an inch or two (2.5 to 5 cm.) above the water surface. A person can easily position him- or herself to deposit a fecal sample on collection structure 20. Three tips 25 will most firmly support collection structure 20 during use since all three tips 25 will naturally engage surface 35 without rocking. The use of a single arm 13 extending toward the front of toilet 30 makes it relatively easy for a user to avoid contaminating the fecal sample with urine.

Figure 6:
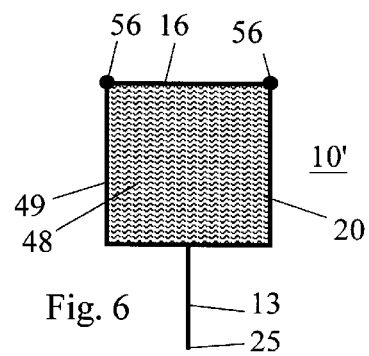
FIG. 6 is a first alternative embodiment of the invention.

Side edges 14 and 15 project past side edge 16 so that the tips 25 can engage surface 35 without interference from the curve of side edge 16. If edge bar 16 is straight as shown in FIG. 6, edge bars 14 and 15 need not project past edge bar 16.

I currently prefer dimensions for collection structure 20 of about 6–10 in. (15–25 cm.) wide (horizontal dimension in FIG. 1) and about 8–10 in. (15×15 cm.) long. I prefer a length for support arm 13 in the range of 4 to 8 in. (10 to 20 cm.) to position collection structure 20 properly within bowl 30. The length of arm 13 should allow collection structure 20 to be located above water line 38 in an approximately horizontal position.

If arm 13 and collection structure 20 are made from any of the common structural plastics, arm 13 and edge bars 14 and 15 can be perhaps 0.125 in. wide (0.3 cm.) by 0.5 in. (1.25 cm.) deep. Interior bars 17 may be somewhat smaller in both width and depth. Adjacent parallel bars 17 may be spaced perhaps 1.0 in. (2.5 cm.) apart.

Figure 4:
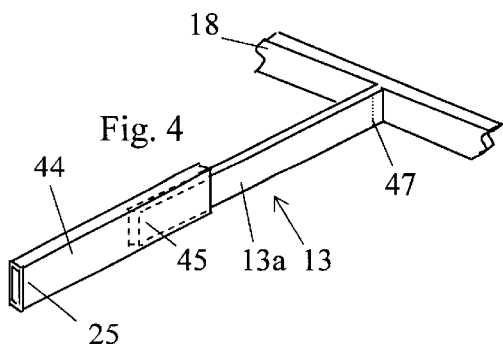
FIG. 4 shows details of a first type of the arm of the article of FIG. 1 for adjusting the length of the arm.

FIG. 4 shows a preferred version of arm 13 in greater detail, with a segment of edge bar 18 shown as well. The cross section of arm 13 is shown with a depth dimension substantially greater than the width dimension. Because of variations in the internal dimensions of various toilet bowls 30, one may sometimes wish to shorten arm 13. Arm 13 comprises a stub arm section 13a attached to the collection structure 20 and a sleeve section 44 having a bore into which the first section can slidingly fit.

In use, sleeve section 44 is slipped to a position on stub arm section 13a that positions article 10 horizontally above water line 38. A score line 47 on stub arm section 13a allows stub section 13a to be easily broken when desired to reduce the size of article 10 for disposal. Sleeve section 44 should fit relatively snugly around stub arm section 13a so that sleeve section 44 slips under moderate force to a position that supports article 10 above water line 38, and at the same time opposes slipping sufficiently to hold sleeve section 44 in the selected position on stub arm section 13a.

Figure 5:
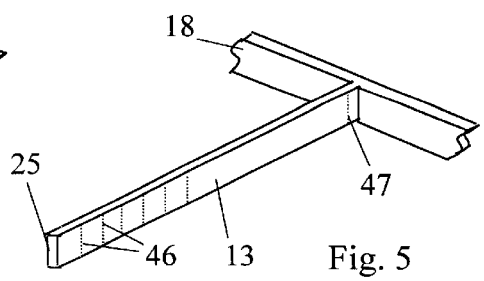
FIG. 5 shows details of a second type of the arm of the article of FIG. 1 for adjusting the length of the arm.

FIG. 5 shows an arm 13 having score lines 46 placed as those shown near the tip 25 of the arm involved where little bending moment and shear load is present during use. Arm 13 can be laterally broken along any one of the score points 45 to adapt article 10 to the size of a particular toilet bowl 30. A score line 47 for reducing the size of article 10 is also shown.

FIG. 6 shows a different version of a fecal collection article 10' having a single arm 13. Article 10' of FIG. 6 has a collection structure 20 having four edge bars 16, 49, etc. A grid material such as fabric or mesh 48 for fecal collection is stretched between the four edge bars 16, 49, etc. Arm 13 has a tip 25 for engaging surface 35 of a toilet bowl 30. Corners 56 provide two further support points for supporting article 10' in a toilet bowl 30.

Figure 7:
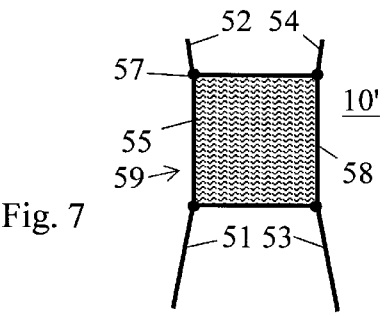
FIG. 7 is a second alternative embodiment of the invention.

FIG. 7 shows a version of the FIG. 1 article 10 having four legs 51, 52, 53, 54 for supporting a rectangular collection structure 59 above water line 38. Edge bars 58, etc. provide structural integrity and support a mesh or grid 55. Fillets as at 57 may be present to stiffen and strengthen connection of each arm 51, 52, 53, 54 to collection structure 59. Four legs may not always provide for totally solid support within every toilet bowl shape. On the other hand, the presence of two legs 51 and 53 may make it easier to avoid contaminating the fecal sample with urine.

Figure 8:
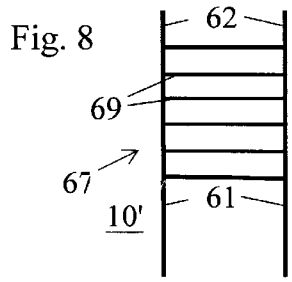
FIG. 8 is a third alternative embodiment of the invention.

FIG. 8 shows an article 10' having a series of parallel bars 69 forming the collection structure 67. Arms 61, 62 are to engage the interior of toilet owl 30. Collection structure 71 comprises a plurality of transverse bars 69. After article 10' has been placed in a toilet bowl 30, two or three layers of toilet paper can be laid on bars 69. The sample may be taken from the stool collected on the toilet paper, and then the toilet paper can be pulled off article 10' to fall into the water in bowl 30. Bars 69 may have a cross section size similar to that of the bars 17 of FIG. 1. Bars 69 may be spaced 0.5–1.0 in. (1.3–2.5 cm.) apart.

The preceding has described my invention; what I desire to protect by Letters Patent is:

1. An article for use in a conventional toilet bowl of the type having an inwardly sloping internal surface and a water line, said article to be supported by the internal surface in a position for collecting a fecal sample discharged by a human into the toilet bowl, said article comprising a collection structure for supporting at least a portion of the fecal sample, said collection structure having a generally planar shape, and having at least one support arm projecting generally outwardly from the collection structure, each said support arm having a tip for engaging the bowl's internal surface for supporting the collection structure above the water line.

2. The article of claim 1, having at least three arms, at least one of which is angularly oriented from two others by at least 90°.

3. The article of claim 1, wherein at least one support arm is generally coplanar with the collection structure.

4. The article of claim 1, wherein the collection structure comprises a relatively rigid peripheral frame integral with each support arm.

5. The article of claim 4, wherein the collection structure comprises a plurality of bars integral with the peripheral frame.

6. The article of claim 1, wherein the cross section of at least one arm includes a feature allowing the arm length to be changed, to allow the article to be conformed to a particular toilet bowl to support the collection structure above the water line.

7. The article of claim 6, wherein the at least one arm includes score points allowing the arm to be selectively bent and broken at each score point.

8. The article of claim 6, wherein at least one arm comprises a stub section attached to the collection structure and a sleeve section having a bore into which the first section can slidingly fit.

9. The article of claim 1, having two pairs of arms each arm in a pair in approximate linear alignment with each other, and each pair of arms approximately parallel with each other.

10. The article of claim 1, wherein the collection structure has a peripheral frame generally defining the plane, and wherein the collection structure comprises a plurality of interior bars having ends unitary with the peripheral frame.

11. The article of claim 10, wherein certain ones of said interior bars are spaced from each other.

12. The article of claim 10, wherein certain ones of said interior bars intersect each other to form a lattice pattern.

13. The article of claim 10, wherein the peripheral frame has four sides, each side intersecting with two other sides to form a collection structure having a generally trapezoidal shape.

14. The article of claim 13, wherein at least one arm projects from an intersection of two sides.

15. The article of claim 14, wherein at least one arm has at least one score point adjacent the tip thereof allowing the arm to be selectively bent and broken at the score point.

16. The article of claim 14, wherein at least one arm has at least one score point adjacent the collection structure, said score point allowing the arm to be selectively bent and broken at said score point, to simplify disposal thereof.

17. The article of claim 1, wherein at least one arm has at least one score point adjacent the collection structure, said score point allowing the arm to be selectively bent and broken at said score point, to simplify disposal thereof.

18. The article of claim 1, wherein at least one arm is non-planar with the collection structure.

\* \* \* \* \*